United States Patent
Hernandez-Pigeon et al.

(10) Patent No.: US 10,765,641 B2
(45) Date of Patent: Sep. 8, 2020

(54) COSMETIC COMPOSITION COMPRISING A COMBINATION OF PONGAMIA OIL AND 4-T-BUTYLCYCLOHEXANOL FOR THE TREATMENT OF ROSACEA

(71) Applicant: PIERRE FABRE DERMO-COSMETIQUE, Boulogne-Billancourt (FR)

(72) Inventors: Hélène Hernandez-Pigeon, Cugnaux (FR); Nathalie Castex-Rizzi, Colomiers (FR); Stéphane Poigny, Saubens (FR); Marie Françoise Aries, Escalquens (FR); Yves Brunel, Marssac-sur-tarn (FR)

(73) Assignee: PIERRE FABRE DERMOT-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 16/475,988

(22) PCT Filed: Dec. 22, 2017

(86) PCT No.: PCT/EP2017/084456
§ 371 (c)(1),
(2) Date: Jul. 3, 2019

(87) PCT Pub. No.: WO2018/127435
PCT Pub. Date: Jul. 12, 2018

(65) Prior Publication Data
US 2019/0350875 A1  Nov. 21, 2019

(30) Foreign Application Priority Data

Jan. 4, 2017  (FR) ...................................... 17 50059

(51) Int. Cl.
| | | |
|---|---|---|
| *A61K 36/486* | (2006.01) | |
| *A61K 31/045* | (2006.01) | |
| *A61P 17/00* | (2006.01) | |
| *A61K 8/34* | (2006.01) | |
| *A61K 8/92* | (2006.01) | |
| *A61K 9/00* | (2006.01) | |
| *A61K 47/10* | (2017.01) | |
| *A61Q 19/00* | (2006.01) | |

(52) U.S. Cl.
CPC .............. *A61K 31/045* (2013.01); *A61K 8/34* (2013.01); *A61K 8/922* (2013.01); *A61K 9/0014* (2013.01); *A61K 36/486* (2013.01); *A61K 47/10* (2013.01); *A61P 17/00* (2018.01); *A61Q 19/00* (2013.01)

(58) Field of Classification Search
CPC .............................. A61K 36/486; A61K 31/045
See application file for complete search history.

(56) References Cited

U.S. PATENT DOCUMENTS

2011/0165136 A1* 7/2011 Babu ...................... A61K 36/87
424/94.1

FOREIGN PATENT DOCUMENTS

| WO | WO 02/074290 A2 | 9/2002 |
|---|---|---|
| WO | WO 2013/182998 A2 | 12/2013 |

OTHER PUBLICATIONS

Author unknown, "Antirougeurs CALM Soothing Mask", URL: http://www.web.archive.org/web/20171117155803/https://www.avene.co.uk/face/products-for-daily-use/redness-prone-skin/antirougeurs-calm-soothing-mask, Nov. 17, 2017, 11 pages.
Author unknown, "Bio-Energizing Cell Repair Balm", Mintel Global New Products Database (DNPD), Record ID: 1425867, Oct. 2010, XP002771237, 14 pages.
Author unknown, "Calm Redness-Relief Soothing Mask", Mintel Global New Products Database(GNPD), Record ID: 5315555, Dec. 2017, XP002779263, 4 pages.
Author unknown, "Karanja Seed Oil 2oz Organic Wild Harvested Cold Pressed FREE travel size NEEM SOAP with purchase", URL:https://www.amazon.com/Karanja-Organic-Harvested-Pressed-purchase/dp/B00DUWWAMG, Jun. 20, 2017, 4 pages.
Author unknown, "Oleo'Sense® Triple action sensory Oléactifs®", Nov. 7, 2014, 10 pages.
Author unknown, "Rosacea Therapy Lotion for Rosacea Conditions", URL: http://web.archive.org/web/20160915063559/http://www.pratimaskincare.com/rosacea-therapy-lotion, Jun. 20, 2017, 1 page.
Author unknown, "SymSitive® 1609 A New Era For Sensitive Skin & Scalp", Mar. 7, 2014, pp. 1-7.
Author unknown, "SYMSITIVE® 1609", URL: https://www.ulprospector.com/de/asia/PersonalCare/Detail/4742/131922/SYMSITIVE-1609, Jun. 20, 2017, 3 pages.
Casas et al., "Quantification de la densité de Demodex folliculorum par PCR dans la rosacée et activation de l'immunité innée", Communications orales, CO070, 2012, pp. B81 (1 page).
Chou et al., "Quantitative Analysis of Dose-Effect Relationships: The Combined Effects of Multiple Drugs or Enzyme Inhibitors", Advances in Enzyme Regulation, Pergamon Press, vol. 22, Jan. 1, 1984, pp. 27-55 (29 pages).
Edwards, "Mechanisms of selective toxicity of metronidazole and other nitroimidazole drugs", Br J Vener Dis, vol. 56, 1980, pp. 285-290, (6 pages).

(Continued)

*Primary Examiner* — Rosanne Kosson
(74) *Attorney, Agent, or Firm* — Birch, Stewart, Kolasch & Birch, LLP

(57) ABSTRACT

The present invention relates to the novel combination of pongamia oil and 4-t-butylcyclohexanol, and to the uses thereof in the fields of cosmetics and dermatology to combat redness.
More specifically, the present invention relates to the cosmetic use of a composition comprising said combination to combat rosacea.

7 Claims, No Drawings

(56) References Cited

OTHER PUBLICATIONS

Facer et al., "Differential expression of the capsaicin receptor TRPV1 and related novel receptors TRPV3, TRPV4 and TRPM8 in normal human tissues and changes in traumatic and diabetic neuropathy", BMC Neurology, vol. 7, No. 11, 2007, pp. 1-12.
Hernandez-Pigeon et al, "Effects of Dextran Sulfate, TRP-Regulin, Pongamia Oil and Hesperidin Methyl Chalcone on Anti-Redness Treatment", IFSCC 2017 Seoul (24 Conference), URL:http://www.iloveweb.kr/IFSCC2017/search/search.html? . . . , Oct. 2017, 1 page.
Hernandez-Pigeon et al, "Effects of Dextran Sulfate, TRP-Regulin, Pongamia Oil and Hesperidin Methyl Chalcone on Anti-Redness Treatment", Journal of Investigative Dermatology, vol. 137, No. 10, Oct. 3, 2017, pp. 1-14.
Hernandez-Pigeon et al., "Effects of TRP-regulin, pognamia oil and hesperidin methyl chalcone on anti-redness treatment", Journal of Investigative Dermatology, vol. 137, 2017, B8, abstract only(1 page).
International Search Report, dated Apr. 20, 2018 for International Application No. PCT/EP2017/084456.
Kueper et al., "Inhibition of TRPV1 for the treatment of sensitive skin", Experimental Dermatology, vol. 19, 2010, pp. 980-986 (7 pages).
Steinhoff et al., "New insights into rosacea pathophysiology: A review of recent findings", J. Am Acad Dermatol, vol. 69, No. 6, Dec. 2013, pp. S15-S26 (12 pages).
Wilkin et al., "Standard classification of rosacea: Report of the National Rosacea Society Expert Committee on the Classification and Staging of Rosacea", J Am Acad Dermatol, vol. 46, 2002, pp. 584-587.

\* cited by examiner

COSMETIC COMPOSITION COMPRISING A COMBINATION OF PONGAMIA OIL AND 4-T-BUTYLCYCLOHEXANOL FOR THE TREATMENT OF ROSACEA

The present invention relates to the novel combination of pongamia oil and 4-t-butylcyclohexanol, and to the uses thereof in the fields of cosmetics and dermatology to combat redness.

More specifically, the present invention relates to the cosmetic use of a composition comprising said combination to combat rosacea.

The skin is the largest organ of the human body, covering nearly 2 m$^2$ of surface area. It plays several fundamental roles, including protection from the outside, thermal regulation and hormone synthesis, and also has an immune function. The skin is made up of three superimposed layers: the epidermis, which is constantly renewed, the dermis and the hypodermis, which provides the fibrous structure. The skin's color, texture and quality also have an undeniable psychosocial function.

All types of sensitive skin are similar in that they react quickly and excessively to changes in temperature, cold, wind, irritating hygiene or toiletries, and inadequate care. Facial redness is the hallmark of sensitive skin, which is characterized by excessive reactivity of the skin and skin vessels. Redness is more or less intermittent, but always unpleasant and embarrassing.

Intermittent redness, also called flushing, is an acute vasodilation reaction that may be due to a commonplace or somewhat "stressful" situation such as a student being called on in class, a job interview, an emotional or combative conversation, but also to a temperature change that increases blood circulation in the face. Food that is too hot, alcoholic beverages and certain foods (spices, mustard, etc.) can also cause redness.

The various factors that can promote and aggravate redness include external factors, such as cold or sunshine, which accelerate skin microcirculation; internal factors, such as emotions, consumption of coffee or spices; heredity. Redness can appear in people with vasoreactive skin, a skin characteristic that may be genetic, or even skin aging: from the age of 25 the skin is more sensitive to rednes.

Redness can eventually become permanent, especially on the cheeks. This is called erythrosis, which is a diffuse but permanent redness most often found on the cheeks in the form of red patches.

Aggravated erythrosis becomes blotchy with the appearance of small dilated vessels.

When pimples appear and the redness becomes permanent, it is called rosacea. Once called "rosacea acne", because in addition to redness, the accompanying pimples recall teenage acne.

Rosacea is a chronic and progressive common inflammatory dermatosis associated with vascular relaxation. It is a condition that affects small vessels in the face. It frequently affects people with fair skin and can have significant psycho-affective consequences. The name of this pathology refers to the characteristic color of the face during the disease. Because the general appearance of the face wrongly suggests chronic overdrinking, rosacea is a disease that, in social terms, is particularly difficult to live with, especially for women. Rosacea is a rather common disease, affecting 2-3% of the adult population in France. Women are particularly affected, as twice as many women as men suffer from rosacea. It mainly affects the central part of the face and is characterized by facial redness or hot flashes, facial erythema, papules, pustules, telangiectasia and sometimes eye lesions called rosacea ocular. In severe cases, especially in men, the soft tissue of the nose can swell and produce a bulbous swelling called rhinophyma. Rosacea progresses, but not necessarily, over several years by flare-ups aggravated by different stimuli such as temperature variations, alcohol, spices, sun exposure or emotions.

The mechanisms of rosacea onset are still very poorly understood today. What scientists do know is that the origin of the disease is vascular. Blood vessels are thought to carry a dysfunction, particularly in Nordic subjects with fair skin, fair eyes and fair hair. This geographical predisposition is found in France, where the disease is very rare in the south and much more frequent in the north of the Loire. On the other side of the Mediterranean, and particularly on dark skin, the disease is practically non-existent.

It is common to classify rosacea into four types according to clinical features according to Wilkin et al., J. Am. Acad. Dermatol. 46(4): 584-587, 2002).

Primary features such as flushing, persistent erythema, papules and pustules, telangiectasia and secondary features such as burning or stinging sensations, plaques, dry skin, edema, ocular manifestations, phymatous changes in rosacea are often observed in association. Based on these signs, patients can be divided into the following four types, although patients may simultaneously exhibit features suggestive of more than one type of rosacea.

Erythematotelangiectatic rosacea is mainly characterized by flushing and persistent central facial erythema. The appearance of telangiectasias is common but not essential for a diagnosis of this type. Central facial edema, burning and stinging sensations and roughness or scaling may also be reported.

Papulopustular rosacea is characterized by persistent central facial erythema with transient papules and/or pustules in a central facial distribution. However, papules and pustules also may occur periorificially, i.e. in the perioral, perinasal or periocular areas. This type of rosacea resembles acne, but comedones are absent. But rosacea and acne can coexist. Patients with this type of rosacea sometimes complain of burning and stinging. This type is often observed before or at the same time as the preceding type, including the presence of telangiectases. The latter may be masked by persistent erythema and papules or pustules.

Phymatous rosacea includes thickening skin, irregular surface nodularities and enlargement. Rhinophyma is the most common presentation, but phymatous rosacea may affect other locations, including the chin, forehead, cheeks and ears. Patients with this type of rosacea also may have patulous, expressive follicles in the phymatous area, and telangiectases may be present. This type is often observed before or at the same time as types 1 or 2. In the case of rhinophyma, these additional *stigmata* may be especially pronounced in the nasal area.

Ocular or ophthalmic rosacea: The diagnosis of ocular rosacea should be considered when a patient's eyes have one or more of the following signs and symptoms: watery or bloodshot appearance, foreign body sensation, burning or stinging, dryness, itching, photosensitivity, blurred vision, telangiectases of the conjunctiva and lid margin, or lid and periocular erythema. Blepharitis, conjunctivitis and irregularity of the eyelid margins are other signs that may be detected. Meibomian gland dysfunction presenting as chalazion or chronic staphylococcal infection as manifested by stye is a common sign of rosacea-related ocular disease.

The diagnosis of ocular rosacea is most often made when cutaneous signs and symptoms are also detected.

Finally, there are other rarer forms of rosacea, in particular granulomatous rosacea.

Despite its frequency, its causes are still poorly determined, and may involve several factors. Diet and climatic factors play a role in the disease and have an impact on these symptoms. In patients with rosacea, there is sometimes a dysfunction of the facial veins, which results in stagnation of blood in the vessels of the face, cascading into dilation of the vessels, edema and alteration of the endothelium.

Corticosteroids can also be incriminated, especially in two situations, the first is rosacea aggravated by the application of corticosteroids. The second is the appearance of the disease following the long-term use of that type of drug, steroidal rosacea.

It has been demonstrated that there is in rosacea a significant increase in the expression of cytokines II-8, II-1b, TNF-α, genes related to the inflammasome (NALP-3 and CASP-1) as well as an increase in the expression of other genes involved in inflammatory and vascular phenomena (Annales de Dermatologie et de Vénéréologie Volume 139, no. 12S page B81 (December 2012)). These cytokines are therefore the marker of choice for monitoring and/or treating this condition.

Oral treatments with tetracycline derivatives are problematic for several reasons but in particular for their significant side effects. Oral administration of tetracyclines such as doxycycline may induce photosensitivity or even phototoxicity or gastrointestinal disorders.

The application WO2002/074290 describes the topical use of at least one non-steroidal anti-inflammatory compound to treat rosacea, compounds which may be combined with a nitroimidazole compound. However, it is reported that the combination of this treatment induces significant side effects, particularly gastrointestinal and renal effects (Edwards, Br. J. Vener Dis., 56, 285-290, 1980).

There is therefore a need for effective active agents in rosacea treatments, which can be used for long periods of time with as few side effects as possible.

The purpose of the present invention is to provide an effective treatment for rosacea. Preferably, this treatment is applied topically, which significantly reduces any systemic side effects.

The present invention thus relates the combination of pongamia oil and 4-t-butylcyclohexanol for use in the prevention and/or treatment of rosacea.

According to a particular embodiment, the combination of pongamia oil and 4-t-butylcyclohexanol is the sole active agent for the prevention and/or treatment of rosacea or for the prevention and/or treatment of skin redness.

The present invention therefore relates to the combination of pongamia oil and 4-t-butylcyclohexanol for use in the prevention and/or treatment of skin redness.

The skin redness may be intermittent redness (i.e. flushing), particularly localized on the cheeks, or erythrosis, particularly localized on the cheeks.

The pongamia or Karanja, Pongamia *pinnata* is a tree of the Fabaceae family. It is widespread in India, Indonesia, Malaysia, Taiwan, Bangladesh, Sri Lanka, southern China, Japan, East Africa, northern Australia and North America. This tree can live in a wide variety of conditions, can survive temperatures from 5° C. to 50° C. and altitudes from 0 to 1200 m. It can grow in almost any type of soil, even low in nitrogen and high in salt, and is drought-resistant. There are a multitude of scientific names for this tree, which shows that this plant comes in a wide variety of forms, which have sometimes been described as different species. The pongamia is up to 18 m high. Its leaves are imperipinnate, 15 to 20 cm long, the leaflets in 2 to 5 pairs, opposite, smooth, shiny, subcoriate. The flowers are white, purplish or pink. The fruit is a woody pod, 35 to 50 mm long, indistinguishable. The seed is unique, compressed, in the shape of a small bean, wrapped in marrow.

Phytochemical examination of the different parts of pongamia shows the presence of specific compounds such as furanoflavones, furanoflavonols, chromenoflavones, furanodiketones.

The seeds contain oil (27-40%), proteins (17-20%), crude fiber (about 14%), amino acids and traces of an essential oil. Other compounds are also found, such as flavones including karanjin and pongamol, chalcones, rotenones, phenol acids, sterols.

The oil in seeds from trees in India contains mainly oleic, linoleic, linolenic and behenic acids. While pongamia seed oil from Pakistan contains myristic, palmitic, stearic, oleic, linoleic, linolenic, arachidic, behenic and lignoceric acid. The unsaponifiable fraction is significant (5.5%). It contains β-sitosterol and other sterols, methyl oleate, 3'-methoxyfurano (2",3":7,8) flavone, karanjin and pongamol which give it a bitter taste as well as other minority molecules belonging to the same series of fluranoflavones: pongapin, kanjone, pongaglabrone, lancolatin B, iso-pongaflavone, pongol and glabrachalcone. Over time the karanjin precipitates, so the older an oil is, the less it contains while the pongamol content remains the same over time.

Pongamia oil is used mainly in India for its anti-parasitic activity in both human and animal therapeutics, but also in agriculture to protect crops against their enemies, insects and nematodes. In human therapy, pongamia oil is applied to the skin to eliminate the scabies parasite. This acaricidal activity has been very developed, it is greater when the oil is combined with ascorbic acid. Different pongamia extracts (oil, or seed, leaf or bark extract) also show repellent activity towards harmful species for several cultivated plants, indeed pongamia extracts have proved effective on about forty harmful species. In addition, pongamia oil has antimicrobial activity on several bacteria of the genera *Bacillus, Micrococcus, Pseudomonas, Staphylococcus, Salmonella, Sarcina, Escherichia* and *Xanthomonas*.

The acaricidal activity identified for pongamia oil is the starting point for its use in rosacea. Pongamia oil is not known to have anti-inflammatory activity, nor in all skin diseases related to inflammation.

4-t-Butylcyclohexanol is an antagonist of transient receptor potential vanilloid-1 (TRPV1). TRPV1 are ionotropic receptors activated by molecules of the vanilloid family such as capsaicin present in chili pepper. TRPV1 are part of the TRP family. This family of receptors is sensitive to mechanical, thermal and certain chemical stimuli. TRPV1 are non-selective cation channel receptors which allow, in response to a stimulus, mostly calcium ions to enter.

TRPV1 are located at the peripheral end of sensitive neurons of small diameter. These are sensory receptors expressed in the skin envelope, mucous membranes and in certain regions of the central nervous system. They are activated by nociceptive heat, low pH, as well as metabolites of oxidized linoleic acids synthesized during burns and generally by other substances belonging to the vanilloid family. When TRPV1 is stimulated, the receptor is activated and changes conformation, which opens the cation channel.

High TRPV1 expression levels have been reported in patients with sensitive skin, while undetectable levels are reported in people without sensitive skin complaints (Facer et al., BMC Neurology, 2007, 7-11.

4-t-Butylcyclohexanol, in formulation with pentylene glycol, is marketed under the name Symsitive® 1609; it is a TRPV1 antagonist, it is stable at pH from 3 to 12 and at temperatures up to 50° C. It is effective for small skin problems, such as tightness and tingling. However, this compound is not known to have activity in inflammation, nor in all skin diseases related to inflammation.

Surprisingly, the inventors discovered that the combination of pongamia oil and 4-t-butylcyclohexanol had an extremely advantageous anti-inflammatory activity (Example 1).

The purpose of the present invention is to provide a treatment for rosacea, which reduces the patient's side effects in particular. Preferably, this treatment is applied topically, which significantly reduces any systemic side effects.

The present invention thus relates to a combination which comprises pongamia oil and 4-t-butylcyclohexanol for use in the treatment and/or prevention of rosacea.

Preferably the 4-t-butylcyclohexanol is in the trans form.

Preferably the 4-t-butylcyclohexanol is solubilized in pentylene glycol.

In an equally preferred way, the 4-t-butylcyclohexanol is solubilized in octyl dodecanol.

The present invention also relates to a combination which comprises pongamia oil and 4-t-butylcyclohexanol for use in the treatment and/or prevention of rosacea, which is selected from the group consisting of erythematotelangiectatic rosacea, papulopustular rosacea, phymatous rosacea and ocular rosacea.

Preferably the 4-t-butylcyclohexanol is in the trans form.

The present invention also relates a combination which comprises pongamia oil and 4-t-butylcyclohexanol for use in the treatment and/or prevention of inflammatory diseases.

The present invention also relates to the use of the combination comprising pongamia oil and 4-t-butylcyclohexanol to prepare a medicinal product to treat and/or prevent rosacea.

Preferably the 4-t-butylcyclohexanol is in the trans form.

The present invention also relates to the use of the combination comprising pongamia oil and 4-t-butylcyclohexanol to prepare a medicinal product to treat and/or prevent inflammatory diseases.

Preferably, the combination according to the invention is applied topically.

Thus, the combination according to one of the embodiments of the invention is characterized in that it is provided in a form suitable for and adapted to topical application.

Topical application refers to application to the skin, the mucous membranes and/or the skin appendages.

The term "treatment of" or "to treat" rosacea or inflammatory diseases means to reduce and/or inhibit the development of rosacea or inflammatory diseases and/or the symptoms thereof.

Symptom of rosacea means persistent redness, burning and stinging, hot flashes or telangiectasia.

Preferably, the present invention also relates to the use of the combination comprising pongamia oil and 4-t-butylcyclohexanol to alleviate and/or prevent redness. The use is preferentially via the topical route and is a cosmetic use.

Redness means more particularly cutaneous redness, intermittent cutaneous redness (i.e. flushing), more particularly localized on the cheeks.

The present invention thus aims at a cosmetic method of attenuation and/or prevention of skin redness comprising the topical application of a combination comprising pongamia oil and 4-t-butylcyclohexanol.

In such a cosmetic method, the skin redness is localized on the cheeks.

The present invention also relates to a cosmetic composition for attenuating and/or preventing skin redness comprising a combination comprising pongamia oil and 4-t-butylcyclohexanol with a cosmetically acceptable excipient, more particularly acceptable for topical application.

Preferably the 4-t-butylcyclohexanol is solubilized in pentylene glycol.

In a preferred manner as well, the 4-t-butylcyclohexanol is solubilized in octyl dodecanol.

In one embodiment of the invention, the cosmetic composition according to is characterized in that the dermatologically or dermocosmetically acceptable excipient comprises a solvent selected from octyl dodecanol, 1,5-pentanediol and at least one vegetable oil. Preferably the solvent is octyl dodecanol or 1,5-pentanediol.

In the present invention, "cosmetically, dermatologically or dermocosmetically acceptable" means that which is useful in the preparation of a cosmetic, dermatological or dermocosmetic composition, which is generally safe, non-toxic and neither biologically nor otherwise undesirable and which is acceptable for therapeutic or cosmetic use, in particular by topical application.

The dermatological, cosmetic and dermocosmetic compositions according to the invention may be in the forms usually known for topical administration, i.e. lotions, foams, gels, dispersions, emulsions, sprays, serums, masks or creams, with excipients allowing in particular skin penetration in order to improve the properties and accessibility of the active principle. Advantageously, it will be a cream, an emulsion.

The invention thus relates to dermatological or dermocosmetic compositions according to one of the embodiments of the present invention, characterized in that they are in a form suitable for and adapted to topical application.

These compositions generally contain, in addition to the compounds of the combination according to the present invention, a physiologically acceptable medium, usually based on water or solvent, for example alcohols, ethers or glycols. They may also contain surfactants, complexing agents, preservatives, stabilizers, emulsifiers, thickeners, gelling agents, humectants, emollients, trace elements, essential oils, fragrances, dyes, matting agents, chemical or mineral filters, moisturizers or geothermal waters, etc.

Typically, the 4-t-butylcyclohexanol is carried and solubilized in a solvent of type fatty alcohol, alkane diol having from 3 to 20 carbon atoms, or a vegetable oil.

The invention thus aims at a combination comprising pongamia oil and 4-t-butylcyclohexanol wherein the 4-t-butylcyclohexanol is solubilized in a solvent of type fatty alcohol, alkane diol having from 3 to 20 carbon atoms, or a vegetable oil. The above-mentioned uses also concern such a combination.

The cosmetically, dermatologically or dermocosmetically acceptable excipient may thus comprise at least one fatty alcohol and/or at least one alkane diol, having from 3 to 20 carbon atoms, and/or at least one vegetable oil.

The alkane diol can thus be selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methyl-pentane-2,4-diol, 1,2-hexanediol, 1,6-hexanediol, 1,2-octanediol, dipropylene glycol, preferably 1,2-butylene glycol, 1,2-pentanediol and dipropylene glycol.

More particularly it is 1,5-pentanediol, also known as pentylene glycol.

The fatty alcohol may be selected from the group of linear or branched fatty alcohols consisting of decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, linoleyl alcohol, linolenyl alcohol, hexyldecanol, octyldodecanol (in particular 2-octyl-1-dodecanol), cetearyl alcohol and behenyl alcohol.

Preferably, it is octyl dodecanol.

The invention thus aims at a combination comprising pongamia oil and 4-t-butylcyclohexanol wherein the 4-t-butylcyclohexanol is solubilized in a solvent selected from octyl dodecanol, 1,5-pentanediol and at least one vegetable oil.

The vegetable oil may be selected from the group consisting of almond oil, groundnut oil, argan oil, avocado oil, safflower oil, coconut oil, rape seed oil, cottonseed oil, wheat germ oil, linseed oil, corn oil, neem oil, hazelnut oil, walnut oil, kernel oil, carnation oil, olive oil, palm oil, pumpkin seed oil, grape seed oil, castor oil, rice oil, sesame oil, soya oil, sunflower oil, microalgae oil.

The cosmetically, dermatologically or dermocosmetically acceptable excipient may also comprise Finsolv TN, or myritol.

Advantageously, the compositions according to the present invention will further comprise Avène water.

These compositions may further contain other active principles leading to a complementary or possibly synergistic effect.

Advantageously, the compositions according to the present invention will comprise 0.01 to 5 wt %, preferably 0.05 to 2 wt %, more preferably 0.1 to 1 wt % pongamia oil based on the total weight of the composition. Preferably the composition will comprise 0.1 wt % pongamia oil based on the total weight of the composition. Equally preferred, the composition will comprise 0.5 wt % pongamia oil based on the total weight of the composition.

Advantageously, the compositions according to the present invention will comprise 0.01 to 5 wt %, preferably 0.05 to 2 wt %, more preferably 0.1 to 1 wt % 4-t-butylcyclohexanol based on the total weight of the composition. Preferably the composition will comprise 0.1 wt % 4-t-butylcyclohexanol based on the total weight of the composition. Equally preferred, the composition will comprise 0.5 wt % 4-t-butylcyclohexanol based on the total weight of the composition.

The dermatological, dermocosmetic or cosmetic compositions and combinations according to the invention may comprise pongamia oil and 4-t-butylcyclohexanol in a 4-t-butylcyclohexanol:pongamia oil mass ratio comprised between 1:10 and 10:1, more particularly 1:1, and even more particularly 1:5.

The invention therefore relates to a combination or a dermatological or dermocosmetic composition for use in the treatment and/or prevention of rosacea as detailed above in which the 4-t-butylcyclohexanol:pongamia oil mass ratio is comprised between 1:10 and 10:1, more particularly 1:1, or even more particularly 1:5.

The invention also relates to a combination or a cosmetic composition for use in the treatment and/or prevention of skin redness, as detailed above, wherein the 4-t-butylcyclohexanol:pongamia oil mass ratio is comprised between 1:10 and 10:1, more particularly 1:1, or even more particularly 1:5.

The invention also relates to a combination or a cosmetic composition for the attenuation and/or prevention of skin redness, as detailed above, wherein the 4-t-butylcyclohexanol:pongamia oil mass ratio is comprised between 1:10 and 10:1, more particularly 1:1, or even more particularly 1:5.

Such compositions can be manufactured according to processes well known to the skilled person.

The following examples illustrate the invention without limiting its scope.

EXAMPLE 1: PHARMACOLOGICAL TEST OF THE COMBINATION OF PONGAMIA OIL AND 4-T-BUTYLCYCLOHEXANOL IN PENTYLENE GLYCOL

The purpose of this study is to evaluate the effects of the combination of pongamia oil and 4-t-butylcyclohexanol in pentylene glycol on the inflammatory response of normal human epidermal keratinocytes in a rosacea environment.

The rosacea environment is mimicked by the mixture of three agonists; an inflammation mediator, an innate immunity mediator and a bacterial component selected from TNF activators, toll-like receptor (TLR2) activators and TRP activators (TRPV1, TRPA1), LL37 peptide, as described in Steinhoff et al. 2013, JAAD.

Protocol

Pongamia oil is evaluated at 10 µg/ml (corresponding to 0.001%), pentylene glycol 4-t-butylcyclohexanol is evaluated at 300 µM (corresponding to 47 µg/ml of 4-t-butylcyclohexanol, and therefore 0.0047%). An IKK inhibitor evaluated at 10 µM was used as positive control.

Human epidermal keratinocytes in a rosacea environment were exposed to the compounds for 25 hours.

The culture supernatant is then removed, centrifuged and frozen at −20° C. IL8 production is quantified by ELISA, according to the supplier's instructions (R&D Systems). A percentage inhibition of IL8 secretion after exposure to the various compounds tested is calculated. The statistical analysis is performed using a one-way analysis of variance (ANOVA) followed by Dunnett's test.

Seven independent experiments are performed and averaged.

Results

The results are summarized in the table below:

|  |  | [IL8] (pg/mL) | SEM | % inh | p |
|---|---|---|---|---|---|
| Vehicle (DMSO) | Control | 69.1 | 5 | — | — |
| Vehicle (DMSO) | Rosacea | 3267.0 | 177 | — | ### |
| IKK | 10 µMM | 515.2 | 41 | 86 | *** |
| Pongamia oil | 10 µg/mL | 2739.5 | 173 | 16 | * |
| PG4B | 300 µM | 2381.8 | 242 | 28 | ** |
| PG4B + pongamia oil | 300 µM + 10 µg/mL | 1667.0 | 199 | 50 | *** |

Inh: inhibition
PG4B: pentylene glycol 4-t-butylcyclohexanol
* $p < 0.05$,
** $p < 0.01$,
*** $p < 0.001$ versus rosacea group,
$p < 0.001$ versus control.

When the keratinocytes are in a rosacea environment, a very clear secretion of IL8 is observed, going from 69±5 µg/mL under control conditions (0.1% DMSO) to 3267±177

μg/mL. The reference inhibitor IKK, which blocks the NFκB pathway, strongly inhibits this IL8 secretion (86% inhibition), thus validating the pharmacological test used.

4-t-Butylcyclohexanol at 300 μM in pentylene glycol statistically significantly inhibits IL8 production. Pongamia oil at 10 μg/mL has a lower inhibitory effect on IL8 secretion, but still in a statistically significant manner. On the other hand, the combination of pentylene glycol 4-t-butylcyclohexanol and pongamia oil at the same concentrations as above inhibits IL8 secretion to a greater extent than with the compounds taken individually, whether with pentylene glycol 4-t-butylcyclohexanol ($p<0.05$) or pongamia oil ($p<0.001$). Thus, the inventors have demonstrated a real synergy on the inhibition of IL8 production with the combination of pentylene glycol 4-t-butylcyclohexanol and pongamia oil. With such activity, this combination has very promising soothing and calming properties.

EXAMPLE 2: EXEMPLARY COMPOSITION ACCORDING TO THE INVENTION

| | |
|---|---|
| Pongamia oil | 0.1 to 1% |
| 4-t-Butylcyclohexanol in pentylene glycol | 0.1 to 1% |
| Sodium hydroxide | 0.1 to 0.5% |
| Capric caprylic/triglyceride | 1 to 5% |
| Poloxamer | 0.5 to 2% |
| Benzoic acid | 0.1 to 0.2% |
| Sodium EDTA | 0.05 to 0.6% |
| C12-C15 benzoate | 1 to 10% |
| Acrylates/C10-30 alkyl crosspolymer | 0.1 to 2% |
| Carbomer | 0.05 to 0.3% |
| Chlorphenesin | 0.1 to 0.3% |
| C14-22 alkyl alcohol | 0.1 to 2% |
| Avene water | qs |

EXAMPLE 3: EXEMPLARY COMPOSITION ACCORDING TO THE INVENTION

| | |
|---|---|
| Pongamia oil | 0.1 to 1% |
| 4-t-Butylcyclohexanol in pentylene glycol | 0.1 to 1%. |
| Sodium hydroxide | 0.1 to 0.5% |
| Tocopheryl acetate | 0.1 to 2% |
| Octyl dodecanol | 2 to 15% |
| Hesperidin methyl chalcone | 0.05 to 0.5% |
| Glycerin | 3 to 10% |
| Sodium EDTA | 0.05 to 0.6% |
| Acrylates/C10-30 alkyl crosspolymer | 0.1 to 2% |
| Hexanediol caprylyl glycol tropolone | 0.2 to 4% |
| Dyes | qs |
| Avene water | qs |

EXAMPLE 4: EXEMPLARY COMPOSITION ACCORDING TO THE INVENTION

| | |
|---|---|
| Pongamia oil | 0.1 to 1% |
| 4-t-Butylcyclohexanol in pentylene glycol | 0.1 to 1%. |
| Acrylate polymer | 1 to 2% |
| C12-C15 benzoate | 2 to 10% |
| Butyl methoxy dibenzoylmethane | 1 to 4% |
| Cetrimonium bromide | 0.01 to 0.5% |
| Potassium cetyl phosphate | 1 to 5% |
| Coco-caprylate/caprate | 2 to 10% |
| Dextran sulfate | 0.2 to 0.5% |
| Dicaprylyl carbonate | 2 to 10% |
| Sodium EDTA | 0.05 to 0.6% |
| Ethylhexyloxyphenol methoxyphenyl | 1 to 5% |
| Glycerin | 3 to 10% |
| Shea butter | 1 to 4% |
| Methicone | 0.5 to 4% |
| Methyl gluceth | 1 to 4% |
| Titanium oxide | 0.2 to 2% |
| Pentylene glycol | 1 to 5% |
| Sorbitol | 1 to 5% |
| Glyceryl stearate | 1 to 3% |
| Tocopheryl glucoside | 0.01 to 0.5% |
| Ethylhexyl triazone | 1 to 5% |
| Fragrances | qs |
| Dyes | qs |
| Avene water | qs |

EXAMPLE 5: EXEMPLARY COMPOSITION ACCORDING TO THE INVENTION

| | |
|---|---|
| Pongamia oil | 0.1 to 1% |
| 4-t-Butylcyclohexanol in pentylene glycol | 0.1 to 1%. |
| C12-C15 benzoate | 2 to 10% |
| Aluminum starch octenylsuccinate | 1 to 3% |
| Butyl methoxy dibenzoylmethane | 1 to 4% |
| Carbomer | 0.05 to 0.3% |
| Cetrimonium bromide | 0.01 to 0.5% |
| Potassium cetyl phosphate | 1 to 5% |
| Coco-caprylate/caprate | 2 to 10% |
| Dextran sulfate | 0.2 to 0.5% |
| Dicaprylyl carbonate | 2 to 10% |
| Sodium EDTA | 0.05 to 0.6% |
| Ethylhexyloxyphenol methoxyphenyl | 1 to 5% |
| Ethylhexyl salicylate | 2 to 5% |
| Glycerin | 3 to 10% |
| Methicone | 0.5 to 4% |
| Methyl gluceth | 1 to 4% |
| Titanium oxide | 0.2 to 2% |
| Pentylene glycol | 1 to 8% |
| Sorbitol | 1 to 5% |
| Glyceryl stearate | 1 to 3% |
| Tocopheryl glucoside | 0.01 to 0.5% |
| Ethylhexyl triazone | 1 to 5% |
| Fragrances | qs |
| Dyes | qs |
| Avene water | qs |

The invention claimed is:

1. A method for treating rosacea or skin redness comprising administering to a patient in need thereof, a composition comprising a therapeutically effective amount of a combination comprising pongamia oil and 4-t-butylcyclohexanol, wherein the 4-t-butylcyclohexanol is solubilized in 1,5-pentanediol.

2. The method according to claim 1, wherein the rosacea is selected from the group consisting of erythematotelangiectatic rosacea, papulopustular rosacea, phymatous rosacea, and ocular rosacea.

3. The method according to claim 1, wherein the administration is topical.

4. A dermatological or dermocosmetic composition comprising a therapeutically effective amount of a combination of pongamia oil and 4-t-butylcyclohexanol, wherein the 4-t-butylcyclohexanol is solubilized in 1,5-pentanediol, in association with at least one dermatologically or dermocosmetically acceptable excipient.

5. The dermatological or dermocosmetic composition according to claim 4, wherein the composition comprises 0.01 to 5 wt % pongamia oil based on the total weight of the composition.

6. The dermatological or dermocosmetic composition according to claim 4, wherein the composition comprises 0.01 to 5 wt % 4-t-butylcyclohexanol solubilized in 1,5-pentanediol based on the total weight of the composition.

7. The dermatological or dermocosmetic composition according to claim 4, wherein the composition is in a form suitable for topical application.

* * * * *